US00PP14205P29

(12) United States Plant Patent
Cherry

(10) Patent No.: US PP14,205 P2
(45) Date of Patent: Oct. 7, 2003

(54) LAVENDER PLANT NAMED 'MADRID PINK IMPROVED'

(50) Latin Name: *Lavandula stoechas L.*
Varietal Denomination: Madrid Pink

(76) Inventor: Robert J. Cherry, RMB 2117 Greta Road, Kulnura, New South Wales 2250 (AU)

( * ) Notice: Subject to any disclaimer, the term of this patent is extended or adjusted under 35 U.S.C. 154(b) by 0 days.

(21) Appl. No.: 10/223,514

(22) Filed: Aug. 19, 2002

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Lavender plant named 'Madrid Pink Improved', characterized by its upright and mounded plant habit; freely branching, dense and bushy plant form; early flowering habit; and purple-colored flower corollas with showy light pink-colored terminal flower bracts.

1 Drawing Sheet

Botanical classification/cultivar designation: *Lavandula stoechas L.* cultivar Madrid Pink Improved.

BACKGROUND OF THE INVENTION

The present Invention relates to a new and distinct cultivar of Lavender plant, botanically known as *Lavandula stoechas L.,* and hereinafter referred to by the name 'Madrid Pink Improved'.

The new Lavender is a product of a planned breeding program conducted by the Inventor in Kulnura, New South Wales, Australia. The objective of the breeding program was to create new Lavender cultivars with large and attractive flowers.

The new Lavender originated from a cross-pollination made by the Inventor of the *Lavandula stoechas L.* cultivar Bella Pink, disclosed in U.S. Plant Pat. No. 12,599, as the female, or seed, parent with the *Lavandula stoechas L.* cultivar Bee Dazzle, not patented, as the male, or pollen, parent. The new Lavender was discovered and selected by the Inventor as a single flowering plant within the progeny of the stated cross-pollination grown in a controlled environment in Kulnura, New South Wales, Australia in 1997.

Asexual reproduction of the new cultivar by terminal cuttings taken at Kulnura, New South Wales, Australia, since 1997, has shown that the unique features of this new Lavender are stable and reproduced true to type in successive generations.

SUMMARY OF THE INVENTION

Plants of the cultivar Madrid Pink Improved have not been observed under all possible environmental conditions. The phenotype may vary somewhat with variations in environment such as temperature and light intensity without, however, any variance in genotype.

The following traits have been repeatedly observed and are determined to be the unique characteristics of 'Madrid Pink Improved'. These characteristics in combination distinguish 'Madrid Pink Improved' as a new and distinct cultivar:

1. Upright and mounded plant habit.
2. Freely branching, dense and bushy plant form.

3. Early flowering habit.
4. Purple-colored flowers with showy light pink-colored terminal flower bracts.

Plants of the new Lavender differ from plants of the parent cultivars and other known Lavender cultivars primarily in flower and terminal bract color, terminal bract size, inflorescence size and peduncle length.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Lavender.

The photograph at the top of the sheet comprises a side perspective view of a typical flowering plant of 'Madrid Pink Improved' grown in a one-gallon container.

The photograph at the bottom of the sheet comprises a close-up view of typical developing inflorescences of 'Madrid Pink Improved' and the upper and lower surfaces of typical leaves.

DETAILED BOTANICAL DESCRIPTION

In the following description, color references are made to The Royal Horticultural Society Colour Chart, 1995 Edition, except where general terms of ordinary dictionary significance are used. Plants were grown under conditions which closely approximate commercial production conditions during the winter and spring in a polycarbonate-covered greenhouse in Lompoc, Calif. Plants used for this description were grown for about 24 weeks in 1-gallon containers and were pinched once. During the production of the plants, day temperatures ranged from 18 to 24° C., night temperatures ranged from 16 to 18° C., and light levels ranged from 4,000 to 8,000 foot-candles.

Botanical classification: *Lavandula stoechas L.* cultivar Madrid Pink Improved.

Parentage:

*Female parent.*—*Lavandula stoechas L.* cultivar Bella Pink, disclosed in U.S. Plant Pat. No. 12,599.

*Male parent.*—*Lavandula stoechas L.* cultivar Bee Dazzle, not patented.

Propagation:

*Type cutting.*—Terminal vegetative cuttings.

*Time to initiate roots.*—Summer: About 7 days at 25° C. Winter: About 14 days at 20° C.

*Time to produce a rooted young plant.*—Summer: About 42 days at 25° C. Winter: About 49 days at 20° C.

*Root description.*—Fine, fibrous, and freely branching.

Plant description:

*Form.*—Perennial. Upright and mounded plant form. Freely branching with lateral branches forming at every node; dense and bushy plant habit; vigorous growth habit. Flowers in verticillasters on crowded spikes with large showy terminal bracts.

*Plant height.*—About 40 cm.

*Plant width.*—About 50 cm.

*Lateral branch description.*—Length: About 32 cm. Diameter: About 5 mm. Internode length: About 1.5 to 2 cm. Texture: Fine pubescence. Color: Young stems: 144B. Older woody stems: 177A to 177B.

*Foliage description.*—Arrangement: Opposite, simple; decurrent. Length: About 3.5 cm. Width: About 5 mm. Shape: Linear, needle-like. Apex: Rounded. Base: Attenuate, clasping. Margin: Entire. Texture, upper and lower surfaces: Fine pubescence. Fragrance: Very aromatic. Venation pattern: Pinnate. Color: Young and fully expanded foliage, upper surface: 147B. Young and fully expanded foliage, lower surface: 147C. Venation, upper surface: 147D. Venation, lower surface: 147C.

Flower description:

*Flower arrangement and shape.*—Small single flowers in verticillasters on crowded spikes. Freely flowering, about eight whorls of ten flowers each per spike; flowers tubular with five lobes; inflorescences with large showy terminal bracts.

*Natural flowering season.*—Continuous throughout the Spring.

*Time to flowering.*—Early flowering habit; plants begin to flower about 12 weeks after planting.

*Flower longevity on the plant.*—Individual inflorescences last about two weeks on the plant and individual flowers last about three days on the plant. Flowers not persistent, terminal flower bracts persistent.

*Flower buds.*—Length: About 6 mm. Diameter: About 2 mm. Shape: Oblong. Color: 79A.

*Inflorescence size.*—Length: About 4 cm. Diameter: About 1.3 cm.

*Flowers.*—Diameter: About 4 by 3 mm. Depth (height): About 1 mm.

*Petals.*—Arrangement: Five, fused into a tube. Length, lobes: About 1 mm. Width, lobes: About 1.5 mm. Tube length: About 1 mm. Shape: Roughly spatulate. Apex: Rounded. Margin: Entire. Texture, upper and lower surfaces: Smooth, velvety. Color: When opening, upper surface: 77A. When opening, lower surface: 77A to 77B. Fully opened, upper surface: 77A. Fully opened, lower surface: 77B to 77C.

*Calyx.*—Arrangement: Five sepals fused into a tube. Length: About 5 mm. Width: About 2 mm. Sepal apex: Acute. Color: Upper surface: 138B. Lower surface: 138B; towards apex, 79D.

*Terminal bracts.*—Arrangement: About four in a single whorl at inflorescence apex. Length: About 1.7 cm. Width: About 7 mm. Shape: Ligulate. Apex: Rounded to slightly acute. Base: Obtuse. Margin: Entire. Texture, upper and lower surfaces: Smooth. Color, upper and lower surfaces: 75B; venation, 77B; color fading to close to white, 155D, with subsequent development.

*Flower bracts.*—Arrangement: Each whorl of flowers subtended by a flower bract. Length: About 7 mm. Width: About 8 mm. Shape: Broadly ovate. Apex: Acute. Base: Truncate. Margin: Entire. Texture, upper and lower surfaces: Smooth. Color, upper and lower surfaces: 147C.

*Peduncle.*—Strength: Strong. Length: About 7 cm. Diameter: About 1 mm. Aspect: Mostly upright. Color: 144D.

*Reproductive organs.*—Stamens: Quantity per flower: Four. Anther shape: Oval. Anther length: Less than 1 mm. Anther color: 173D. Pollen amount: Scarce. Pollen color: 173D. Pistils: Quantity per flower: One. Pistil length: About 5 mm. Stigma shape: Rounded. Stigma color: 71B. Style length: About 4 mm. Style color: 77D. Ovary color: 144C.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2 to 40° C.

It is claimed:

1. A new and distinct cultivar of Lavender plant named 'Madrid Pink Improved' as illustrated and described.

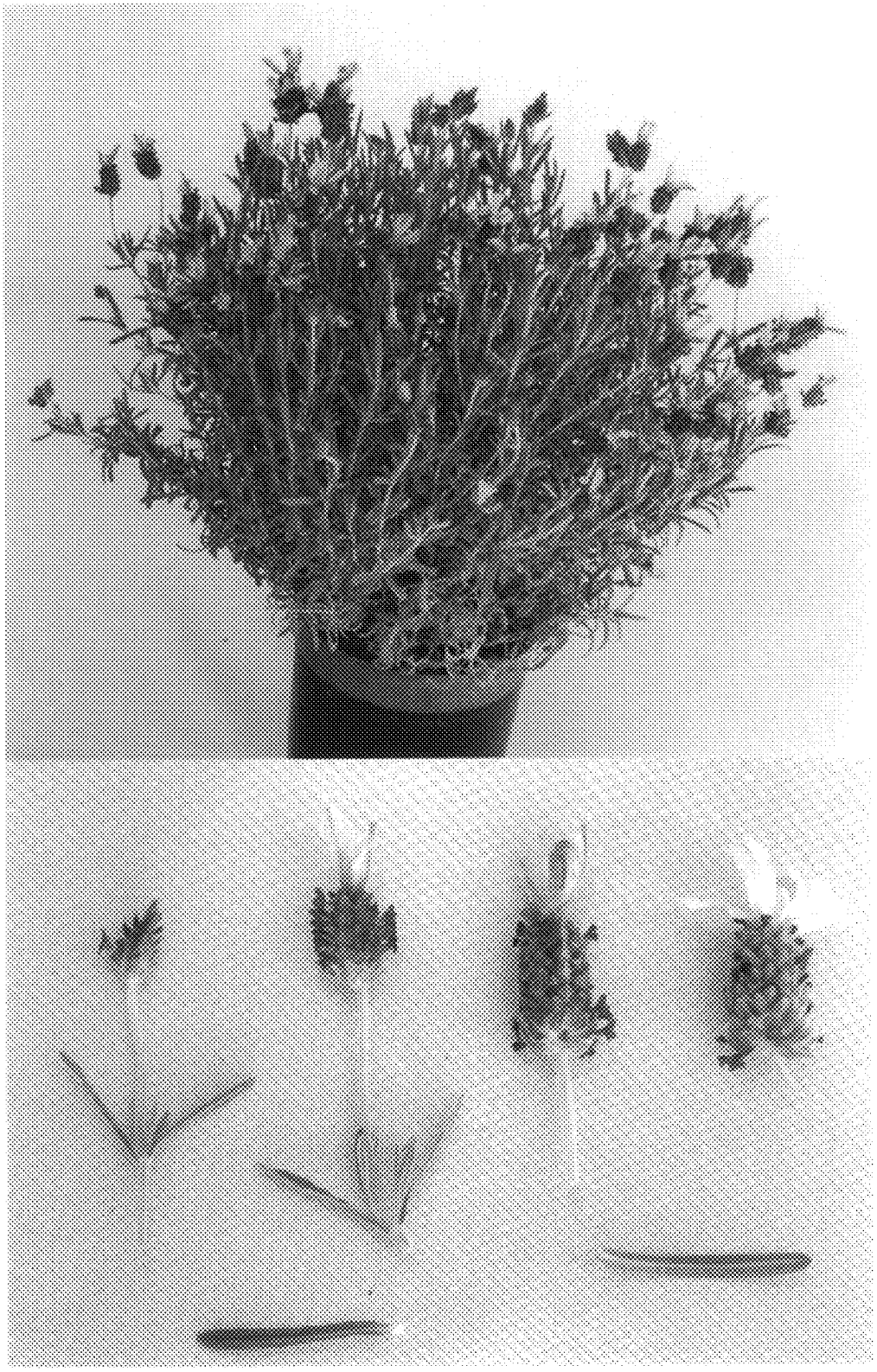

* * * * *